United States Patent [19]

Myllymäki

[11] Patent Number: 5,515,858
[45] Date of Patent: May 14, 1996

[54] WRIST-HELD MONITORING DEVICE FOR PHYSICAL CONDITION

[76] Inventor: Matti Myllymäki, Sisämaantie 18 A, Fin-02610 Espoo, Finland

[21] Appl. No.: 290,971

[22] PCT Filed: Feb. 26, 1993

[86] PCT No.: PCT/FI93/00067

§ 371 Date: Aug. 24, 1994

§ 102(e) Date: Aug. 24, 1994

[87] PCT Pub. No.: WO93/16636

PCT Pub. Date: Sep. 2, 1993

[30] Foreign Application Priority Data

Feb. 28, 1992 [FI] Finland .................................. 920896

[51] Int. Cl.$^6$ ...................................................... A61B 5/11
[52] U.S. Cl. ................... 128/670; 128/690; 128/774
[58] Field of Search ........................ 128/670, 690, 128/739, 782, 630, 715, 773, 774, 661.07, 668, 687

[56] References Cited

U.S. PATENT DOCUMENTS

| | | | |
|---|---|---|---|
| 3,742,937 | 7/1973 | Manuel et al. ......................... | 128/690 |
| 4,059,979 | 11/1977 | Mackie et al. ......................... | 72/342 |
| 4,090,504 | 5/1978 | Nathan ................................... | 128/670 |
| 4,450,843 | 5/1984 | Barney et al. ......................... | 128/670 X |
| 4,799,491 | 1/1989 | Eckerle ................................. | 128/690 X |
| 4,819,860 | 4/1989 | Hargrove et al. ..................... | 228/668 |
| 4,938,228 | 7/1990 | Righter et al. ......................... | 128/690 |
| 4,952,928 | 8/1990 | Carroll et al. ......................... | 340/825.54 |
| 4,958,645 | 9/1990 | Cadell et al. ......................... | 128/903 |
| 5,025,791 | 6/1991 | Niwa ..................................... | 128/670 |
| 5,301,154 | 4/1994 | Suga ..................................... | 128/690 X |
| 5,413,116 | 5/1995 | Radke et al. . | |

FOREIGN PATENT DOCUMENTS 5332765  3/1978  Japan .................................. 128/670

*Primary Examiner*—Sam Rimell
*Attorney, Agent, or Firm*—Weingarten, Schurgin, Gagnebin & Hayes

[57] ABSTRACT

The present invention relates to a wrist-held monitoring device for independently observing the physical condition of a person by means of motoric activity or movement and physiological conditions, e.g., temperature and/or electric conductivity of the skin. The anomalous condition data is transmitted by conventional techniques on a radio frequency message to one or more receivers, which either set off a local alarm or further transfer the data by conventional techniques to a centralized receiving point for alarm generation there.

8 Claims, 4 Drawing Sheets

WRIST-HELD MONITORING DEVICE FOR PHYSICAL CONDITION

FIELD OF THE INVENTION

This invention relates to wrist-held monitoring devices, and more particularly to wrist-held monitoring devices that monitor movement and physiological condition.

BACKGROUND OF THE INVENTION

A wrist-held device for the independent and on-line surveillance of movement and physical condition is not yet available. Traditionally, the surveillance of patient movement out of a region has been effected by using extra-personal sensors, e.g. by monitoring the use of a door. The problems include a long monitoring time, high installation costs as well as false alarms as a person under surveillance leaves the space without switching off the surveillance. There are also portable radio transmitters provided with a switch for indicating the posture of a person. A problem with such devices are false alarms as the user must remember to take off the device when lying down. Another problem is that some surveillance is only active when a person is on his or her feet.

Prior monitoring devices are capable of monitoring the heart, however such devices do not provide information about motoric activity and are not suitable for personal motion control or surveillance. The heart monitoring devices are also traditionally expensive and require frequent battery replacement. Such devices are also not suitable for applications with many users in a restricted area or when long-term surveillance is required.

SUMMARY OF THE INVENTION

An object of the invention is to provide a wrist-watch type of device, which the carrier wears constantly on his or her wrist and which monitors physiological condition independently and on-line as well as issues an alarm upon detecting an abnormal situation. The wrist-held device delivers an alarm, which carries an ID-code specifying the transmitting device, to a separate receiver or a plurality of receivers which can even cover an entire hospital or region. The receivers can be connected to various local alarms or to an emergency phone. The device may also offer the user an opportunity to set off a self-induced alarm with a press button.

Condition surveillance by means of motoric activity and physiological condition is a main function of the device. The device is capable of achieving a so-called functional time surveillance for the elderly, i.e., incidents where a person being monitored falls, loses consciousness or the ability to move will be identified and the device automatically produces an alarm. All active sensing and the processing of sensor messages take place in a wrist alarm unit with a simple and very low-current technique, the device being operable for very long periods on the same batteries.

DESCRIPTION OF THE DRAWINGS

The invention will now be described in more detail with reference made to the accompanying drawings, in which.

DETAILED DESCRIPTION OF THE INVENTION

Figure 1:
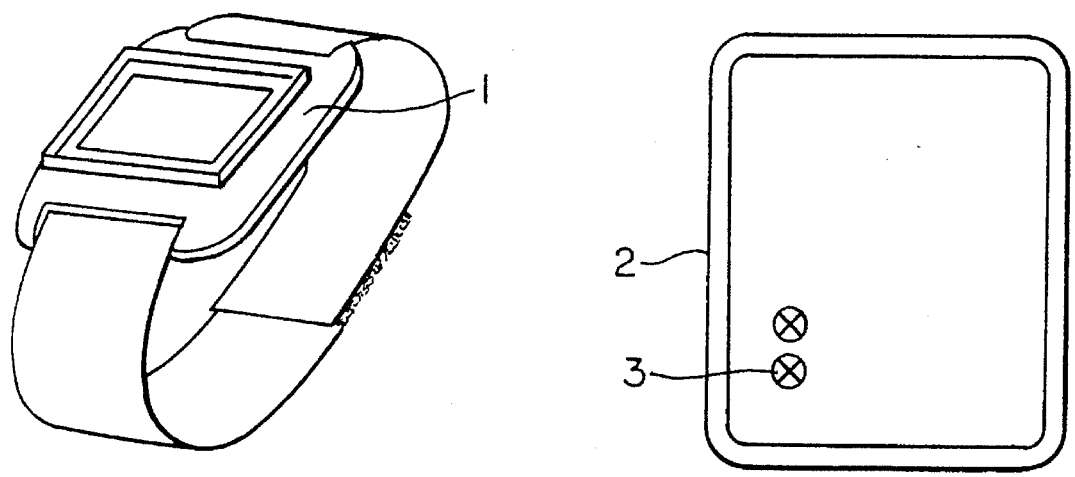
FIG. 1 shows a device of the invention, including a wrist-held detector and transmitter unit and a separate receiver unit.
Figure 2:
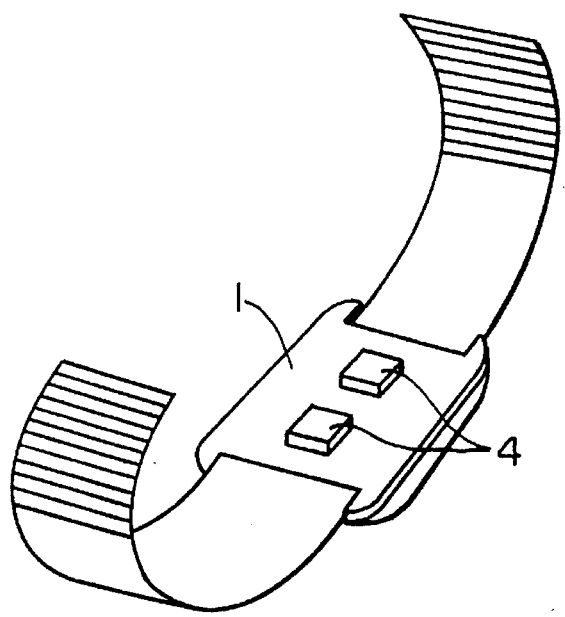
FIG. 2 is a bottom view of the detector and transmitter unit.

Referring to FIG. 2, a device of the invention includes a wrist-watch size detector and transmitter unit 1, whose bottom is fitted with silver-plated contact surfaces for a sensor 4 of temperature and/or electric conductivity of the skin. Alternatively or in addition, the sensor 4 may include a sensor which detects or indicates a heartbeat. When monitoring the heart operation, one heartbeat or pulse interval is sufficient during any watching period when no motion pulse is being counted by means described below, in order to reduce the current consumption. The device is also provided with an acceleration sensor 5, and a pulse detector 6 for the acceleration sensor, a counter 7A for counting the pulses from detector 6, a fuzzy logic circuit 7 for handling and analysis of the information obtained from sensors 4 and 5, and a radio transmitter 9. The alarm conditions are interpreted on the basis of the sensor signals by means of the fuzzy logic as will be explained below. A separate receiver unit 2 is fitted with an alarm relay release 11 and a radio receiver 10.

Figure 3:
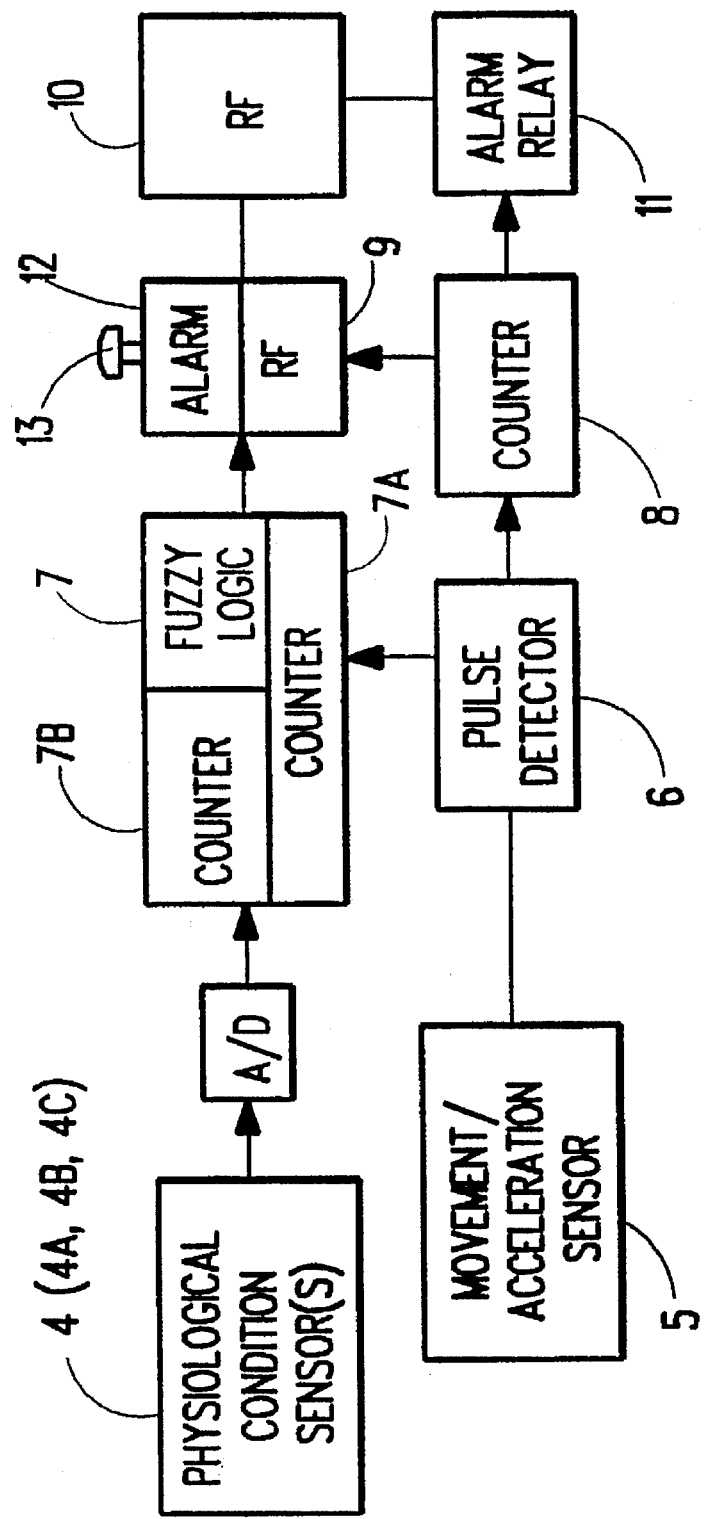
FIG. 3 shows a general block diagram for a device of the invention.

Referring now to FIG. 3, the electric skin conductivity and/or temperature of skin is measured with contact surfaces of sensors 4. After A/D transformation, the signal from sensor 4 is measured by counter 7B. By means of fuzzy logic 7, for example, the electric skin conductivity may be used to control the counting rate of counter 7A in a manner that a high skin resistance decelerates the counter 7A and a low skin resistance accelerates the counter 7A, thereby defining alarms within sliding alarm limits.

Figure 4:
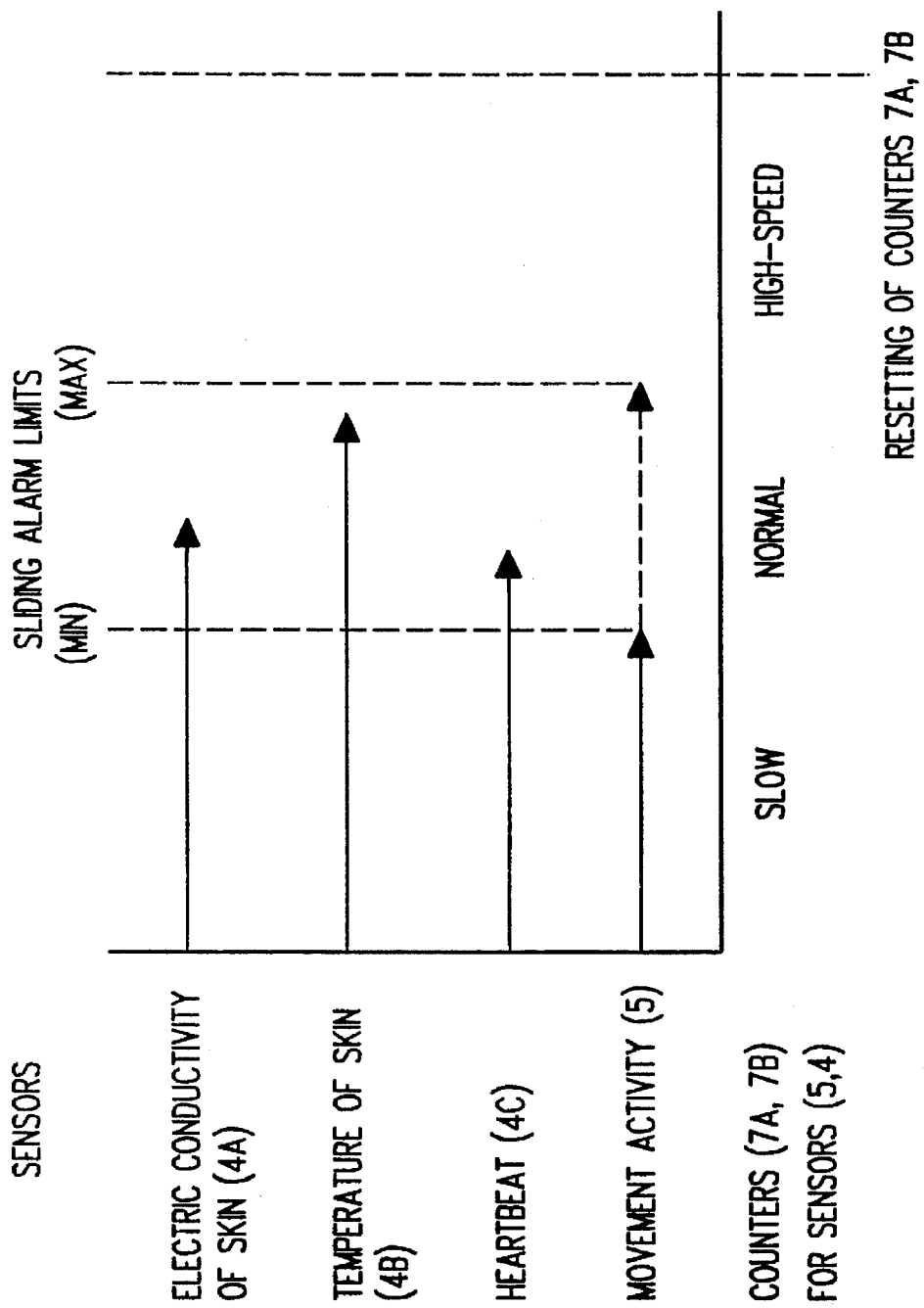
FIG. 4 shows how fuzzy logic is applied to interpret the mutual dependency of the different sensors.

Referring now to FIG. 4, the fuzzy logic 7 controls the mutual dependency of the different sensors 4 and 5 such that by means of a signal from acceleration sensor 5 an estimate of movement activity is made, and this estimate is used to determine the sliding alarm limits (Min and Max) for signals from sensor(s) 4. If the counting value of counter 7B for one or more of the sensors 4 falls outside these sliding alarm limits (Min and Max) in a watching period, then an alarm is caused first in an alarm unit 12 of the wrist held device and, if the alarm is not deactivated in a predetermined time by pressing button 13, then the alarm is transmitted to receiver 10. If the counting value(s) of counter 7B is (are) within these limits, then the counters 7A, 7B are reset to zero to begin a new watching period.

Acceleration sensor 5 detects hand movements and uses pulse detector 6 also to deliver a pulse to the fuzzy logic 7 whenever a sufficiently extensive movement is detected. If it is not reset to zero by this pulse within a determined period of time, the counter 7A will switch on radio transmitter 9 which sends an alarm to receiver 10. So, in addition to the general movement activity, the acceleration sensor 5 may be used to indicate the rate of acceleration of individual hand movements.

A counter 8 is used to count a predetermined number of pulses delivered by the acceleration sensor 5 so as to switch on radio transmitter 9 and to send a so-called dementia message reporting that a monitored person is moving. If a receiver defining the area to be monitored receives such a message, an alarm will be released. When a user takes off the wrist alarm, the contact surfaces measuring electric conductivity and/or temperature of the skin set the counter rate to such a slow level that an alarm is not released if a user removes the device e.g. when having a shower or sauna. When leaving home, the device is retained on the wrist beyond detection and, thus, false alarms are not produced as a result of even a long absence.

Figure 5:
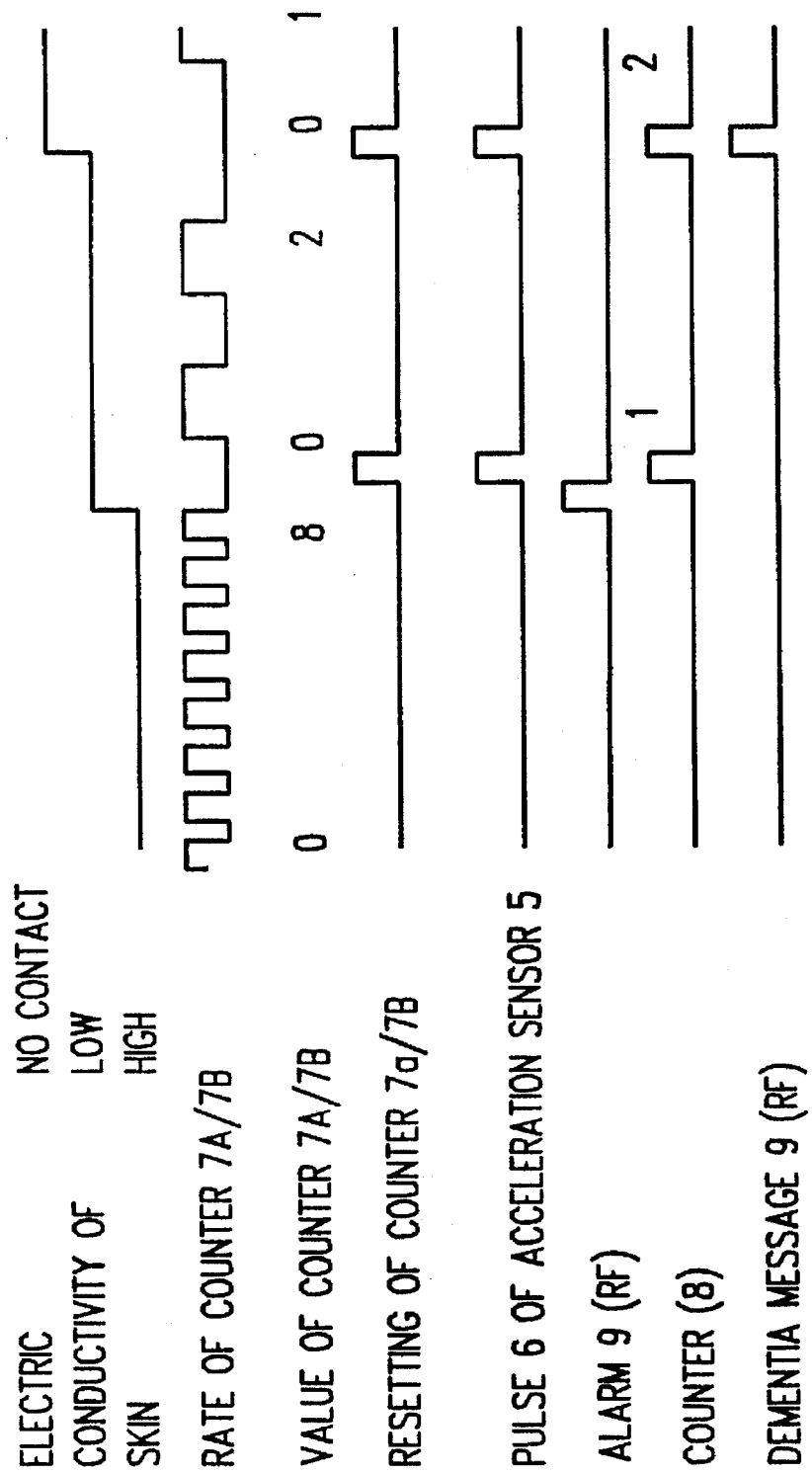
FIG. 5 shows an example of a logical flow chart for signals and pulses associated with operation of the device.

An example of the logical operation of wrist alarm 1 and detectable factors of the device are illustrated in FIG. 5. As illustrated in FIG. 5, the controlling signal for a wrist alarm is electric conductivity of the skin, which is obtained from contact surfaces 4 controlling the rate of counter 7A, whereby a high electric conductivity of the skin results in the counter reaching an alarm threshold in counter 8 more quickly, the alarm switching on radio transmitter 9. When a user is moving his or her hand, the acceleration sensor 5 delivers a reset pulse to counter 7A and counting is restarted from the beginning. Counter 8 transmits a dementia message after receiving a sufficient number of pulses.

Although the invention has been shown and described with respect to an illustrative embodiment thereof, it should be appreciated that the foregoing and various other changes, omissions and additions in the form and detail thereof may be made without departing from the spirit and scope of the invention as delineated in the claims.

I claim:

1. A monitoring device for simultaneously monitoring physical condition and movement, comprising:
    a wrist-held detector and transmitter unit, comprising a detector, comprising
        a first sensor for monitoring physiological condition;
        a second sensor for monitoring movements; and
        a fuzzy logic circuit in electrical communication with said first sensor and said second sensor;
    a radio transmitter in electrical communication with said fuzzy logic circuit; and
    a first alarm in electrical communication with said fuzzy logic circuit; and
    a receiver unit for receiving a radio signal from said radio transmitter, said receiver unit including a second alarm.

2. The monitoring device of claim 1, wherein said fuzzy logic circuit controls said first sensor and said second sensor such that output from one of said first sensor and said second sensor sets sliding alarm limits for output from the other of said first sensor and said second sensor.

3. The monitoring device of claim 1, wherein said first sensor detects physiological conditions selected from the group consisting of skin temperature, skin electrical conductivity, and heartbeat rate.

4. The monitoring device of claim 1 further comprising a first counter in electrical communication with said first sensor and said fuzzy logic circuit, said first counter capable of switching on said radio transmitter.

5. The monitoring device of claim 1, further comprising a pulse detector and a second counter, said pulse detector in electrical communication with said first counter and said second counter and said second sensor, said second counter capable of switching on said radio transmitter.

6. The monitoring device of claim 3, wherein said first counter is decelerated by high electrical resistance of the skin, and accelerated by low electrical resistance of the skin.

7. The monitoring device of claim 1, wherein said second sensor is an acceleration sensor.

8. The monitoring device of claim 1, wherein said second sensor measures the rate of acceleration of individual hand movements.

* * * * *